(12) United States Patent
Schaub

(10) Patent No.: US 11,547,516 B2
(45) Date of Patent: Jan. 10, 2023

(54) HOLDING DEVICE FOR HOLDING A PORTABLE MEDICAL APPLIANCE

(71) Applicant: Markus Schaub, Wetzlar (DE)

(72) Inventor: Markus Schaub, Wetzlar (DE)

(*) Notice: Subject to any disclaimer, the term of this patent is extended or adjusted under 35 U.S.C. 154(b) by 834 days.

(21) Appl. No.: 16/286,772

(22) Filed: Feb. 27, 2019

(65) Prior Publication Data

US 2019/0269477 A1 Sep. 5, 2019

(30) Foreign Application Priority Data

Mar. 1, 2018 (DE) ...................... 10 2018 104 663.4

(51) Int. Cl.
*A61B 50/20* (2016.01)
*A61B 50/31* (2016.01)
*A61G 12/00* (2006.01)
*A61B 90/57* (2016.01)

(52) U.S. Cl.
CPC .............. *A61B 50/20* (2016.02); *A61B 50/31* (2016.02); *A61B 90/57* (2016.02); *A61G 12/00* (2013.01)

(58) Field of Classification Search
CPC ......... A61B 50/20; A61B 50/31; A61B 90/57; A61G 12/00; A47B 96/14; A47B 96/067; A47B 96/1408; A47B 96/1433; A47F 5/0838; A47F 5/0846; A47F 5/08; B25B 11/00
USPC .......... 211/70.6, 85.13, 94.01; 248/500, 510, 248/222.13, 222.11, 221.11, 223.41; 269/289 R, 291
See application file for complete search history.

(56) References Cited

U.S. PATENT DOCUMENTS

| | | | | |
|---|---|---|---|---|
| 2,688,504 A * | 9/1954 | Parker | ................. | B61D 45/001 403/80 |
| 3,204,776 A * | 9/1965 | Brown | ................. | B25H 3/04 248/222.41 |
| 3,330,525 A * | 7/1967 | Weinstein | ................. | A47G 1/202 211/116 |
| 3,591,121 A * | 7/1971 | Parris | ................. | B65D 19/0002 248/346.02 |
| 3,613,900 A * | 10/1971 | Chiu | ................. | A47B 9/08 211/186 |
| 4,094,415 A * | 6/1978 | Larson | ................. | A47F 5/0823 211/85.15 |
| 4,213,593 A * | 7/1980 | Weik | ................. | B64D 11/0696 248/501 |
| 4,230,432 A * | 10/1980 | Howell | ................. | B60P 7/0815 410/105 |

(Continued)

*Primary Examiner* — Jennifer E. Novosad
(74) *Attorney, Agent, or Firm* — Clark & Brody LP

(57) ABSTRACT

A holding device for holding a portable medical appliance and for introducing it into a mounting rail includes a main body with a main face and at least one guide element having a guide profile, the at least one guide element being formed along a longitudinal axis of the main body and extending from the main body in an insertion direction. The at least one guide element is introducible into a guide in the mounting rail. The holding device also includes at least one fixing member for fixing the portable medical appliance to the holding device via an adapter, a locking mechanism that is movable at least partially in the insertion direction between a first and second locking positions, and at least one clamping mechanism, the clamping mechanism being movable at least partially in the insertion direction between first and second clamping positions.

12 Claims, 9 Drawing Sheets

(56) References Cited

U.S. PATENT DOCUMENTS

| | | | | |
|---|---|---|---|---|
| 4,256,424 A * | 3/1981 | Knox | B60P 7/0815 | 410/104 |
| 4,359,163 A * | 11/1982 | Ratti | B23Q 3/15553 | 211/70.6 |
| 4,496,271 A * | 1/1985 | Spinosa | B64C 1/20 | 410/105 |
| 4,509,649 A * | 4/1985 | Evans | B25H 3/00 | 403/374.4 |
| 4,527,760 A * | 7/1985 | Salacuse | F16B 21/02 | 248/108 |
| 4,568,050 A * | 2/1986 | Radoy | A47B 57/565 | 211/187 |
| 4,602,756 A * | 7/1986 | Chatfield | F16M 11/045 | 403/80 |
| 4,805,784 A * | 2/1989 | Solheim | A47F 5/0846 | 211/94.01 |
| 4,826,022 A * | 5/1989 | Duarte | A47F 5/0846 | 248/222.12 |
| 4,853,555 A * | 8/1989 | Wheat | H01R 25/16 | 725/76 |
| 5,384,103 A * | 1/1995 | Miller | A61L 2/26 | 206/508 |
| 5,681,539 A * | 10/1997 | Riley | A61B 50/22 | 206/370 |
| 5,732,965 A * | 3/1998 | Willey | B62J 17/04 | 280/288.4 |
| 5,941,430 A * | 8/1999 | Kuwabara | A41H 19/00 | 206/382 |
| 6,244,447 B1 * | 6/2001 | Frieze | A61L 2/26 | 206/370 |
| 6,375,017 B1 * | 4/2002 | Schattner | A61M 5/1418 | 604/80 |
| 6,443,316 B1 * | 9/2002 | Mao | A47L 19/04 | 211/74 |
| 6,579,503 B1 * | 6/2003 | Tanamal | A61L 2/26 | 206/370 |
| 6,637,605 B2 * | 10/2003 | Ernst | B25H 3/003 | 206/378 |
| 6,945,414 B1 * | 9/2005 | Stevens | A47F 5/0846 | 211/183 |
| 6,948,895 B2 * | 9/2005 | Buff | B61D 45/001 | 410/97 |
| 7,017,898 B2 * | 3/2006 | Varzino | B25B 1/22 | 269/43 |
| 7,066,341 B1 * | 6/2006 | Hartford | A61L 2/26 | 211/85.13 |
| 7,175,152 B2 * | 2/2007 | Dittmer | F16M 13/02 | 248/222.51 |
| 7,198,158 B2 * | 4/2007 | Kao | A47F 5/083 | 211/70.6 |
| 7,601,312 B2 * | 10/2009 | Riley | A61B 50/33 | 248/684 |
| D612,216 S * | 3/2010 | McQuary | D7/637 | |
| 7,669,945 B2 * | 3/2010 | Blersch | F25D 23/067 | 108/107 |
| 7,703,866 B2 * | 4/2010 | Benz | F25D 25/02 | 312/348.3 |
| 7,722,837 B2 * | 5/2010 | Riley | A61B 50/33 | 206/370 |
| 7,789,248 B1 * | 9/2010 | Salerno | A47G 25/08 | 211/106.01 |
| 7,861,860 B2 * | 1/2011 | Bettenhausen | A61L 2/26 | 206/439 |
| 7,975,979 B2 * | 7/2011 | Bishop | B64D 11/0696 | 248/500 |
| 8,011,071 B2 * | 9/2011 | O'Brien | A61M 16/1075 | 248/221.11 |
| 8,069,998 B2 * | 12/2011 | Thomas | A61B 50/34 | 206/370 |
| 8,172,188 B2 * | 5/2012 | Dubinskiy | B62J 9/23 | 248/221.11 |
| 8,267,246 B2 * | 9/2012 | Bettenhausen | A61B 50/30 | 206/439 |
| 8,459,472 B2 * | 6/2013 | Hofman | A47F 5/0815 | 211/106.01 |
| 8,517,361 B2 * | 8/2013 | Sambuceto | B25B 5/003 | 269/37 |
| 8,522,986 B2 * | 9/2013 | Kitchen | B25H 3/04 | 248/220.31 |
| 8,636,154 B2 * | 1/2014 | Chinn | A61G 3/0891 | 211/106.01 |
| 8,727,118 B1 * | 5/2014 | Chen | B25H 3/022 | 206/374 |
| 8,807,496 B2 * | 8/2014 | Kessler | F16M 11/041 | 396/428 |
| 8,827,219 B2 * | 9/2014 | Kessler | F16M 11/041 | 396/428 |
| 9,581,782 B2 * | 2/2017 | Abby | H04Q 1/064 | |
| 9,611,975 B2 * | 4/2017 | Chinn | B60R 11/06 | |
| 9,692,194 B2 * | 6/2017 | Chinn | F16B 21/09 | |
| 9,944,217 B2 * | 4/2018 | Schroeder | B60P 7/0815 | |
| 10,391,190 B1 * | 8/2019 | Oko | F16B 5/0614 | |
| 10,398,239 B1 * | 9/2019 | Luberto | A47F 5/0025 | |
| 10,405,676 B1 * | 9/2019 | Underwood | F16B 1/00 | |
| 10,518,024 B2 * | 12/2019 | Grindinger | B65B 39/006 | |
| 10,527,219 B2 * | 1/2020 | Carnevali | F16M 13/02 | |
| 10,676,196 B2 * | 6/2020 | Pacheco | B64D 11/0619 | |
| 10,835,339 B2 * | 11/2020 | Krensky | A61B 50/3001 | |
| 11,090,127 B2 * | 8/2021 | Oko | A61B 50/33 | |
| 11,214,374 B2 * | 1/2022 | Lucas | B64D 11/0619 | |
| 2005/0161421 A1 * | 7/2005 | Bienick | A47B 96/028 | 211/194 |
| 2006/0171651 A1 * | 8/2006 | Laursen | H04Q 1/062 | 385/135 |
| 2008/0000853 A1 * | 1/2008 | Huang | B25H 3/04 | 211/70.6 |
| 2009/0014584 A1 * | 1/2009 | Rudduck | B64D 11/0696 | 244/118.6 |
| 2012/0085720 A1 * | 4/2012 | Bettenhausen | A61B 50/34 | 211/85.13 |
| 2012/0126075 A1 * | 5/2012 | Chinn | F16M 13/02 | 248/221.11 |
| 2013/0081233 A1 * | 4/2013 | Lu | B60P 7/0815 | 24/185 |
| 2013/0108503 A1 * | 5/2013 | Ramkhelawan | A61B 50/34 | 422/1 |
| 2014/0048503 A1 * | 2/2014 | Gwag | A47F 5/0846 | 211/162 |
| 2014/0374564 A1 * | 12/2014 | Schroeder | B60P 7/0815 | 248/503 |
| 2015/0129524 A1 * | 5/2015 | Cushion | A61B 50/34 | 29/466 |
| 2015/0223898 A1 * | 8/2015 | Merlo | F16M 13/022 | 211/85.13 |
| 2015/0251311 A1 * | 9/2015 | Huang | F16B 21/04 | 211/70.6 |
| 2017/0209318 A1 * | 7/2017 | Schroeder | F16M 13/022 | |
| 2019/0269477 A1 * | 9/2019 | Schaub | A61B 50/20 | |

* cited by examiner

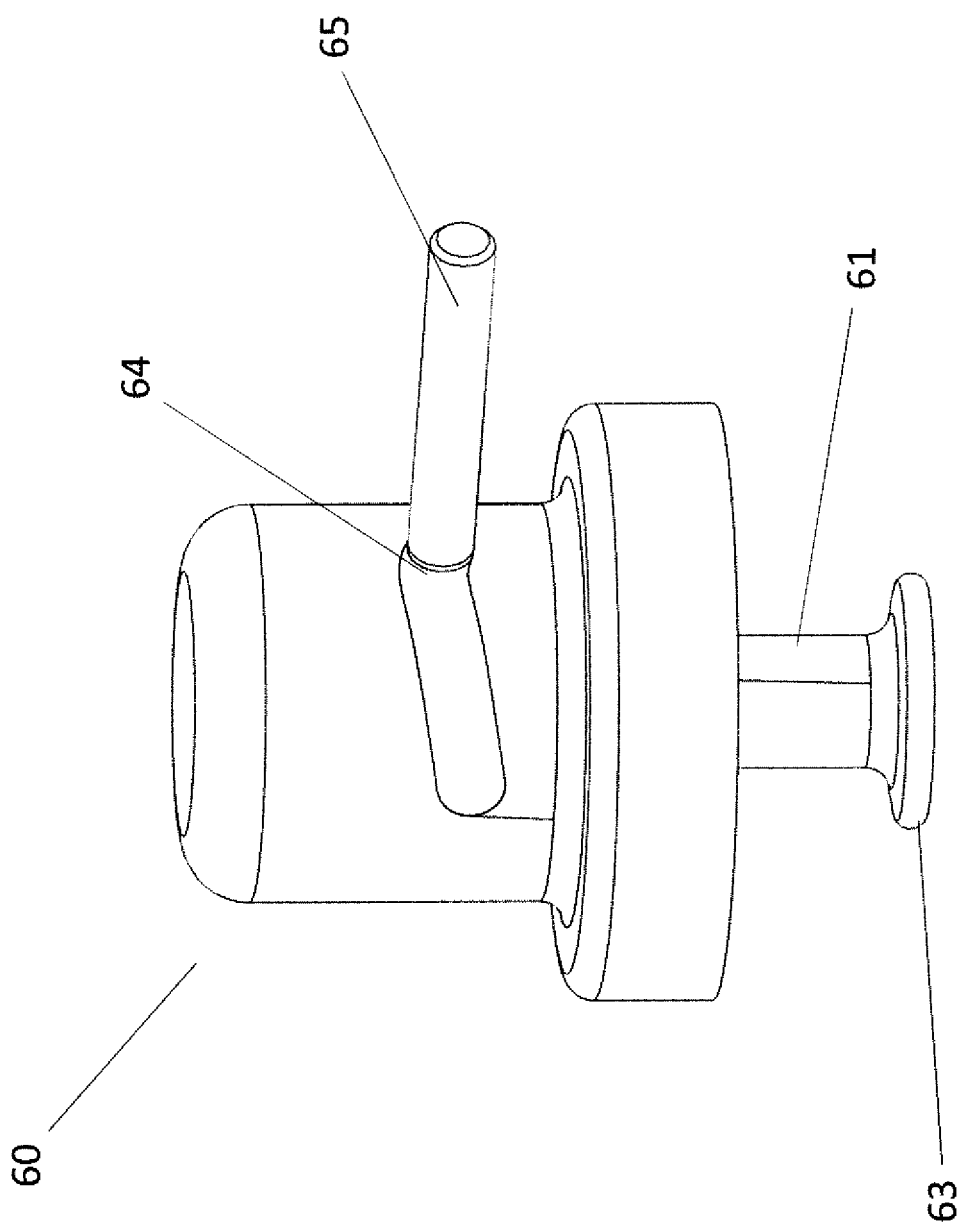

HOLDING DEVICE FOR HOLDING A PORTABLE MEDICAL APPLIANCE

The invention relates to a holding device for holding a portable medical appliance and for introducing into a mounting rail according to the preamble of claim 1.

A holding device of this type can be used for fastening portable medical appliances for example when transporting patients in ambulances and/or rescue vehicles on land, in the water or especially in the air. Portable medical appliances should be understood here as meaning all appliances and devices of which the primary areas of application are in nursing and emergency medicine. Patient carrier systems can thus also be understood to be included thereby.

Many of the medical appliances used in transporting patients require additional parts such as cables, belts, tubes, batteries or the like. As a rule, for better portability by the emergency personnel and for protecting the often delicate and movable parts, the appliances are packed in cases or bags, wherein the appliances can take up a volume of up to 100 liters in the packed state. The appliances are in this case relatively heavy and accordingly not easy to handle. Portable medical appliances belong as a rule to the equipment of emergency and rescue vehicles, which also include associated helicopters or boats. In a rescue mission, the patient is often administered emergency treatment with the associated appliance in situ.

Very frequently, the appliances are also part of a resuscitation process and thus vital for the patient's survival. Therefore, it is important that no unnecessary time is wasted for putting together or acquiring the appliances. This already starts with the removing or possibly the dismounting of the packed appliance from the relevant rescue vehicle. Clear, easy and few hand movements are highly advantageous here. In mobile medical and rescue work, the emergency personnel thus always has to be able to reach all necessary appliances and equipment quickly and reliably, said personnel often only having one hand free because they are frequently already carrying other cases, bags or the like. Accordingly, any holding device that can be released easily is advantageous.

Before and after use and during journeys to missions in which a particular medical appliance does not need to be used, the corresponding medical appliance has to be able to be fixed securely in the transport space in order to prevent the risk of injury during the journey or flight as a result of the sometimes heavy appliances falling over. Furthermore, the protection of the appliances also requires secure fastening during transport. This is intended to be ensured by the fastening device secured to the vehicle in question.

Furthermore, especially mobile intensive care is faced with the problem that there is often little space available. Therefore, it is important that all appliances and devices be able to be stowed in a space-saving manner. Thus, holding devices for portable medical appliances that take up little space represent a further advantage.

Various holding devices for portable medical appliances for fixing the appliances in question are available on the market. The holders known from the prior art generally require a large amount of space, are complicated to operate and are not suitable for ensuring quick, easy, space-saving and secure fixing of portable medical appliances.

Therefore, the invention is based on the object of providing a holding device for holding a portable medical appliance, which allows secure fixing and rapid removal of a medical appliance.

According to the invention, the abovementioned object is achieved by holding devices for holding a portable medical appliance and for introducing into a mounting rail in that the holding device has a main body with a main face, and at least one guide element having a guide profile, the at least one guide element being formed along a longitudinal axis of the main body and extending from the main body in an introduction direction. Furthermore, the holding device has at least one fixing means for fixing the portable medical appliance to the holding device via an adapter, a locking means that is movable at least partially in the insertion direction between a first locking position and a second locking position, and at least one clamping means, the at least one clamping means being movable at least partially in the insertion direction between a first clamping position and a second clamping position.

In this case, the mounting rail can be attached to a wall both vertically and horizontally. Diagonal orientations are also conceivable. Accordingly, the holding device according to the invention can be moved vertically or horizontally along the wall, depending on how the mounting rail is oriented on the wall. Thus, space-saving attachment of the holding device is ensured in an advantageous manner, because the system of mounting rail and holding device is not limited to just one orientation of the mounting rail.

The medical appliances can be appliances from different manufacturers. The appliances are either configured to be directly compatible with the holding device or are equipped with a compatible adapter. The particular dimensions of the appliances are already taken into consideration during the production of the holding device according to the invention. The exact dimensions of the individual holding devices thus depend, inter alia, on the appliances for which they have been produced and are accordingly not essential to the invention.

No protection is claimed for the mounting rail itself; it can be produced by third parties. The rail is in particular attached fixedly to a wall, for example screwed, welded, adhesively bonded, etc. The main body should in any case be formed in a relatively rigid and durable manner, for example as a metal plate. Fixing, locking, and clamping means are arranged largely on a top side of the main face of the main body, wherein these means can extend through the main body to an underside of the main face.

Arranged on the underside of the main face is the at least one guide element with the guide profile, wherein in particular two guide elements are provided, which are formed parallel to one another and along the longitudinal axis of the main body. The guide elements extend from the underside of the main face of the main body in the introduction direction, i.e. point substantially in a direction opposite to the direction in which the fixing, locking, and clamping means are directed. According to the invention, the guide profile of the at least one guide element is configured such that it can cooperate with the particular mounting rail. In this case, provision is made for the holding device to be movable along the longitudinal axis of the mounting rail as long as it is not locked and/or clamped to the mounting rail. To this end, the at least one guide element is introduced into corresponding receiving regions of the mounting rail. As soon as the holding device has been introduced into the mounting rail in this way, it can be moved in a guiding direction relative to the rail.

The locking means, which is formed on the top side of the main face, serves in particular to lock the holding device in a desired position relative to the mounting rail such that the holding device can still be moved in the introduction direction but is no longer movable along the mounting rail in the guiding direction. By releasing the locking mechanism, the holding device is movable in the introduction direction again.

If the holding device has been locked in a desired position, it can be clamped immovably with the aid of the at least one clamping means. In this state, the holding device can no longer be moved in any direction—it is now fully but releasably fastened.

Fastened to the portable medical appliance is an adapter, which is connected to the holding device via the at least one fixing means. This connection can be for example a screw connection, weld, clamped connection, adhesive bond or the like. In this case, in particular three separate fixing means are provided. The adapter makes it possible to use different medical appliances with the same holding device system. As soon as the medical appliance or the adapter has been connected to the holding device via the fixing means, the medical appliance can be held on the mounting rail by being fastened to the holding device. By releasing the holding device from the mounting rail, the medical appliance can be used. Furthermore, the medical appliance can be introduced into a guide in the mounting rail via the holding device, wherein the at least one guide element of the holding device is movable in the guiding direction along the mounting rail. Via interaction between the locking means and clamping means, the holding device can be fastened in a desired position along the mounting rail. The holding device is prevented from moving in the guiding direction by the locking means. The holding device is prevented from moving in the introduction direction by the at least one clamping means.

A holding device configured in accordance with the invention has the advantage that a corresponding medical appliance can be fastened securely within a space (for example ambulance, rescue helicopter etc.). In this way, it is also possible to withstand forces, as usually arise during rescue missions on land, in the air or water, without the medical appliance slipping. In particular, it is possible, by way of the fixing means, to prevent the medical appliance from undesirably dropping out of the holding device. The guide element, clamping means and locking means in turn ensure that the holding device is connected immovably to the mounting rail.

According to a practical development of the invention, the guide profile of the at least one guide element has, in a guiding direction, a profile pattern with regularly alternating wide portions and narrow portions, the guide profile having clearances for receiving the locking means and the at least one clamping means. The profile pattern of the at least one guide of the mounting rail is in this case configured in a substantially complementary manner to the profile pattern of the guide profile of the holding device. As a result, the guide profile can be fitted without problems in the mounting rail in the insertion direction. The regularly alternating wide portions and narrow portions of the at least one guide profile (and thus also of the at least one complementary guide) have in this case the advantage that, as a result of the holding device being moved in the guiding direction, the holding device is prevented from dropping out of the mounting rail. Only when the wide portions and narrow portions of the guide profile are congruent with the wide portions and narrow portions of the guide again can the holding device be released from the mounting rail. The guide profile according to the invention thus allows prefixability of the holding device to the mounting rail.

It may also be intended for the holding device to have a first guide element with a first guide profile, a second guide element with a second guide profile, a first clamping means, and a second clamping means, the first guide element having a clearance for receiving the locking means and a clearance for receiving the first clamping means, and the second guide element having a clearance for receiving the second clamping means. By way of the clearances in the guide elements, clamping means and locking means can be received in the guide elements. In this case, provision can be made in particular for the clamping means and locking means to be able to extend from the main body in the direction of the guide profile. In this way, the clamping means and the locking means can be moved from a first position into a second.

In a variant of the holding device, the locking means extends out of the main body in the introduction direction in its first locking position. In this position, the locking means can latch in place in a wide portion of the guide of the mounting rail. This prevents the holding device from being able to move in the guiding direction along the mounting rail.

According to an advantageous configuration, an underside of the locking means is positioned entirely inside the main face of the main body in the second locking position. In this position, the holding device can be moved in the guiding direction along the mounting rail. Only when the locking means has been brought into the first position does it latch or engage in a wide portion of the guide of the mounting rail and prevent the holding device from being able to move.

As provided in one embodiment, it is also advantageous when the locking means of the holding device has the same cross profile as one of the wide portions of the at least one guide profile. Such a configuration has the result that the locking means can latch in place with a precise fit in the wide portion of the guide of the mounting rail. This prevents the holding device from moving relative to the mounting rail, for instance by wobbling. Furthermore, an engagement of the locking means with a precise fit in the guide of the mounting rail increases the degree of fastening of the holding device to the mounting rail.

A further advantage results from the variant in which the clearance in the at least one guide element for receiving the locking means in its first locking position is located at least partially in a region of the at least one guide profile in which the profile pattern has a narrow portion. The locking means latches in its first position in a wide portion of the guide of the mounting rail. Since the clearance in the guide element for receiving the locking means is located at least partially in a region of the guide profile in which the profile pattern provides a narrow portion, the guide element and guide are moved relative to one another soon as the locking means engages in a wide portion of the guide of the mounting rail. Because the profile pattern of the at least one guide element and that of the at least one guide are formed preferably in a complementary manner to one another and because the wide portions and narrow portions of the profile pattern are formed preferably in a regularly alternating manner, the latching of the locking means in place in a wide portion of the guide of the mounting rail results in particular in the profile pattern of the at least one guide element and the profile pattern of the at least one guide being positioned in an offset manner with respect to one another—each narrowing of the at least one guide of the mounting rail coincides with a wide portion of the at least one guide element and each wide portion of the at least one guide of the mounting rail coincides with a narrow portion of the at least one guide element.

Provision can also be made for the clearance in the at least one guide profile for receiving the at least one clamping means to be located at least partially in a region of the guide profile in which the profile pattern has a wide portion. This ensures in a simple manner that the holding device can be introduced into the mounting rail.

According to an advantageous embodiment, the at least one clamping means can have a clamping face that is parallel to the main face of the main body, the clamping face being in the form of a flange. In this case, provision is preferably made for the clamping face of the clamping means to be formed in a manner corresponding to the profile pattern of the at least one guide element, such that the clamping face complements the profile pattern of the guide profile when the guide element is seen in flat view.

The fact that the at least one clamping means is located at least partially in a region of the guide profile in which the profile pattern provides a wide portion has the result that the clamping face of the at least one clamping means coincides with a narrow portion of the at least one guide of the mounting rail as soon as the locking means engages, in its first position, in a wide portion of the guide of the mounting rail.

According to one development of the holding device according to the invention, it is also advantageous when, in the first clamping position, the clamping face of the clamping element is at a smaller distance from the main body than in the second clamping position, the clamping means clamping the holding device immovably to the mounting rail in the first clamping position. The configuration of the clamping means thus results in the advantage that the holding device is firmly clampable to the mounting rail. When the holding device has been introduced into the mounting rail, it can first of all be moved in the guiding direction along the rail as long as the at least one clamping means is in its second position and the locking means is in its second position. As soon as the locking means has been brought into its first position, it can engage or latch in place in a wide portion of the at least one guide of the mounting rail. Once the latching means has latched in place, the profile pattern of the at least one guide element of the holding device and the profile pattern of the at least one guide of the mounting rail are arranged in an offset manner with respect to one another. In this state, the clamping face of the at least one clamping means coincides with a narrow portion of the at least one guide of the mounting rail. If the clamping means is now moved from its second position into its first, the clamping face is moved in the direction of an inner wall of the guide until the clamping face bears firmly against the wall. This causes the holding device to be clamped to the mounting rail, this ensuring, in addition to the locking by the locking means, that the holding device is fastened reliably to the mounting rail.

Furthermore, provision can be made for the at least one guide profile to have a bottom face, which is substantially parallel to the main face of the main body, and for the clamping face of the clamping means to be more or less flush with the bottom face in the second clamping position. As a result, it is possible to ensure that the holding device can be guided and moved along the mounting rail in the guiding direction because a planar or smooth bottom face of the guide profile reduces the friction that prevails between the region of the guide profile and the mounting rail when the holding device is moved in the guiding direction relative to the mounting rail.

According to a preferred variant, the locking means has a toggle lever mechanism with a lever and a spring element, the locking means being able to be adjusted from the first locking position into the second locking position and/or from the second locking position into the first locking position via the toggle lever mechanism. Such a mechanism allows easy and quick operation of the locking means. In particular, the locking of the holding device to the mounting rail can be performed or released with only one hand movement. The spring element serves in this case to pretension the locking means. The locking means can—when it is in its first locking position—be moved at least partially counter to the spring force of the spring element in the direction of the second position of the locking means. The spring force in this case always acts on the locking means in the direction of its first locking position. The locking means is thus pushed by the spring element in the direction of its first locking position, in which the locking means can engage in the guide of the mounting rail as soon as it is guided to a sufficiently large recess in the guide of the mounting rail. This ensures that the holding device can be guided along the mounting rail until the locking means latches in place at one point on the guide of the mounting rail.

Provision can furthermore be made for the at least one clamping means to have a rotary mechanism with a handle, via which the clamping means can be adjusted from the first clamping position into the second clamping position and/or from the second clamping position into the first clamping position. A rotary mechanism allows quick and uncomplicated actuation of the at least one clamping means in a simple manner. In this way, the holding device can be clamped reliably and especially firmly to the mounting rail.

A further advantage that arises from the toggle lever mechanism and the rotary mechanism is the fact that the locking means and the at least one clamping means, respectively, are actuated without additional tools.

In an alternative embodiment, the at least one fixing means is a threaded bolt. A threaded bolt ensures that the holding device can be connected as stably as possible to the adapter that is fastened to the medical appliance.

Further features, details and advantages of the invention can be gathered from the wording of the claims and from the following description of exemplary embodiments with reference to the drawings, in which:

FIG. 9 shows a perspective view of a clamping means in a preferred embodiment.

Figure 1:
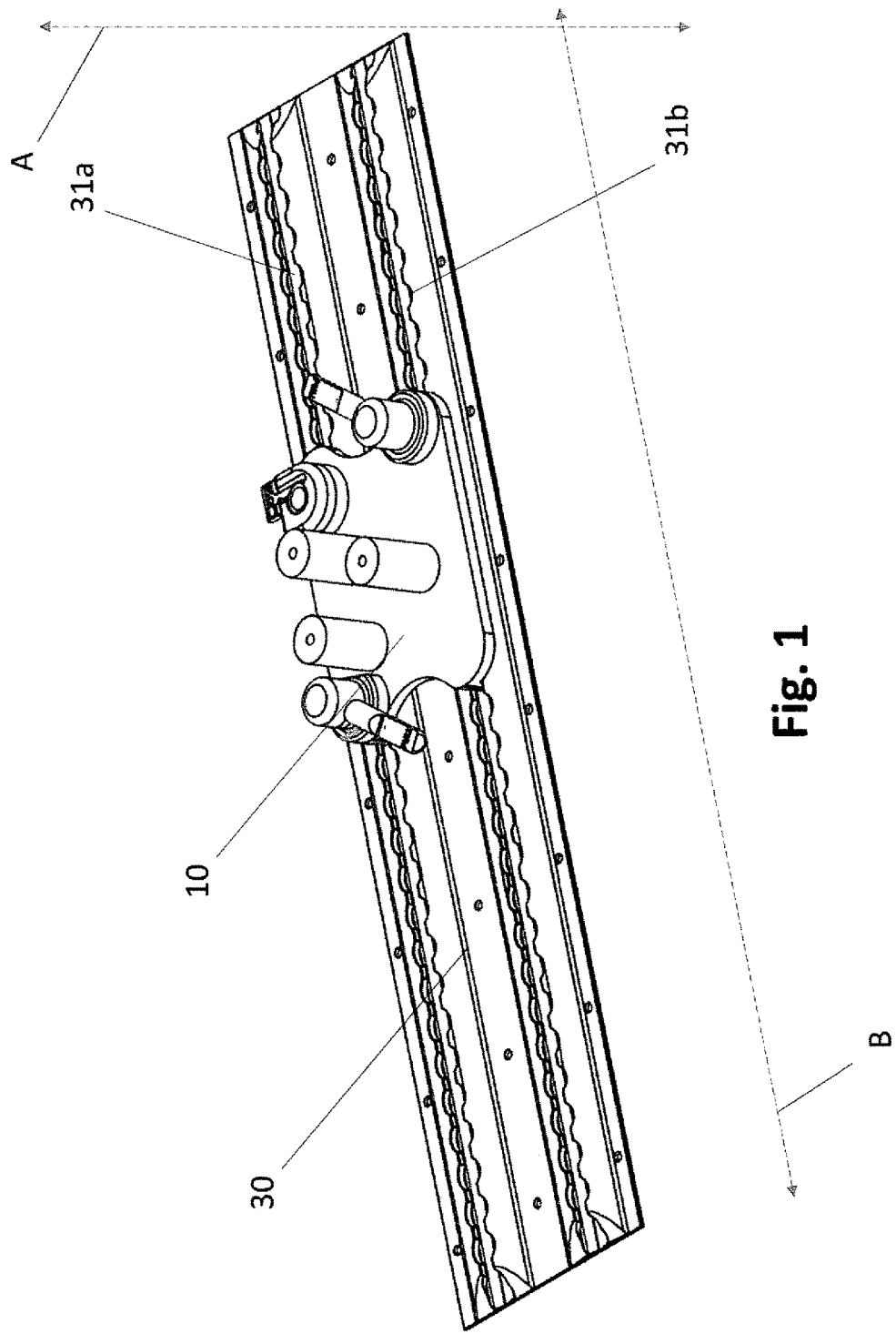
FIG. 1 shows a perspective view of a preferred embodiment of the holding device according to the invention for holding a portable medical appliance and for introducing into a mounting rail in a fixed state.

FIG. 1 shows a perspective view of a preferred embodiment of the holding device 10 according to the invention for holding a portable medical appliance and for introducing into a mounting rail 30 in a fixed state. Such a holding device 10 is suitable for example for fixing, fastening or holding portable medical appliances when transporting patients in ambulances and/or rescue vehicles on land, in the water or especially in the air. Portable medical appliances should be understood here as meaning all appliances and devices of which the primary areas of application are in nursing and emergency medicine. Patient carrier systems can thus also be understood to be included thereby. FIG. 1 shows how one variant of the holding device 10 according to the invention has been introduced into a mounting rail 30 and fixed thereto such that the device cannot be removed from the mounting rail 30 in an introduction direction A or be moved in a guiding direction B. The mounting rail 30 can, as shown by way of example in FIG. 1, have two guides each with a guide profile, which are able to receive the at least one guide element 40 of the holding device 10 (not shown in FIG. 1).

Figure 2:
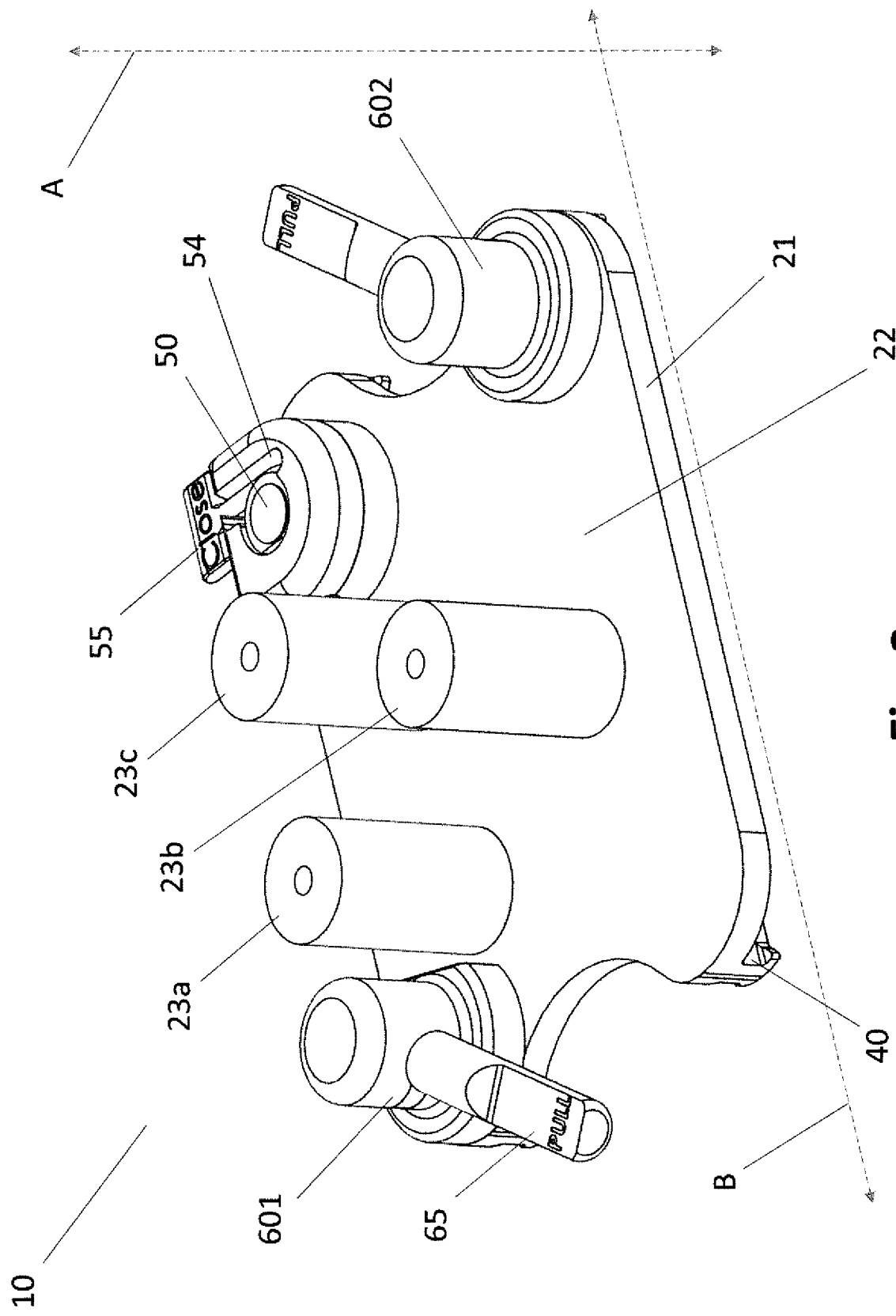
FIG. 2 shows a perspective view of the holding device according to FIG. 1 without the mounting rail.

FIG. 2 shows a perspective view of the holding device 10 from FIG. 1 without the mounting rail 30. The holding device 10 shown in FIG. 1 and FIG. 2 has three fixing means 23a, b, c, wherein the fixing means 23a, b, c are configured as cylindrical bolts each with an internal thread. An embodiment with more or fewer than three fixing means 23a, b, c is also conceivable. The fixing means 23a, b, c configured as threaded bolts are, according to the variant in FIG. 1 and FIG. 2, attached in a central position to the main face 22, preferably by adhesive bonding or welding. However, other embodiments can be provided in which the at least one fixing means 23 is attached to the main face 22 of the holding device 10 in a peripheral position.

FIG. 1 and FIG. 2 also show a locking means 50. The locking means 50 is in a first position 51 (not discernible in FIG. 1 and FIG. 2). The locking means 50 preferably has a toggle lever mechanism 54 with a lever 55 and a spring element, wherein the locking means 50 can be adjusted from the first locking position 51 into a second locking position 52 and/or from the second locking position 52 into the first locking position 51 via the toggle lever mechanism 54. Such a mechanism allows quick and easy operation of the locking means 50. In particular, the locking of the holding device 10 to the mounting rail 30 can be performed or released with only one hand movement. According to the variant in FIG. 1 and FIG. 2, the lever 55 is recessed into the mount of the locking means 50 as soon as the locking means 50 is in its first position. By pulling on the lever 55, it can be hinged out of the mount, with the result that the locking means 50 is moved from the first position into the second via the lever mechanism. Solutions are also conceivable in which hinging the lever 55 out ensures that the locking means 50 is moved from its second position into the first.

The holding device 10 illustrated in FIG. 1 and FIG. 2 also has a first clamping means 601 and a second clamping means 602, wherein embodiments with more or fewer than two clamping means 60 are also possible. As shown in FIG. 1 and FIG. 2, the locking means 50, clamping means 601, 602, and fixing means 23a, b, c are each attached to the same side, facing away from the mounting rail, of the main face 22 of the holding device 10, preferably by adhesive bonding, screwing or by welding. The clamping means 601, 602 each have a rotary mechanism with a handle 65, via which the clamping means 601, 602 can be adjusted from a first clamping position 61 into a second clamping position 62 and/or from the second clamping position 62 into the first clamping position 61. The rotary mechanism allows quick and uncomplicated actuation of the particular clamping means 601, 602. In this way, the holding device 10 can be clamped reliably and especially firmly to the mounting rail 30. Provision is made in particular here for the handle 65 to be able to be moved along a diagonally formed recess in the mount of each particular clamping means 601, 602, with the result that the distance of the handle 65 from the main face 22 is reduced or increased. Because the handle 65 is connected fixedly to the clamping means 601, 602, the clamping means 601, 602 accordingly moves along therewith, with the result that a clamping face 63 (not illustrated in FIG. 1 and FIG. 2) of the clamping means 60 reduces or increases its distance from the main body 21 of the holding device 10. This yields the advantage that the holding device 10 is able to be clamped firmly to the mounting rail 30 via the clamping means 601, 602. In FIG. 1 and FIG. 2, both handles 65 are each at a maximum distance from the main body.

Figure 3:
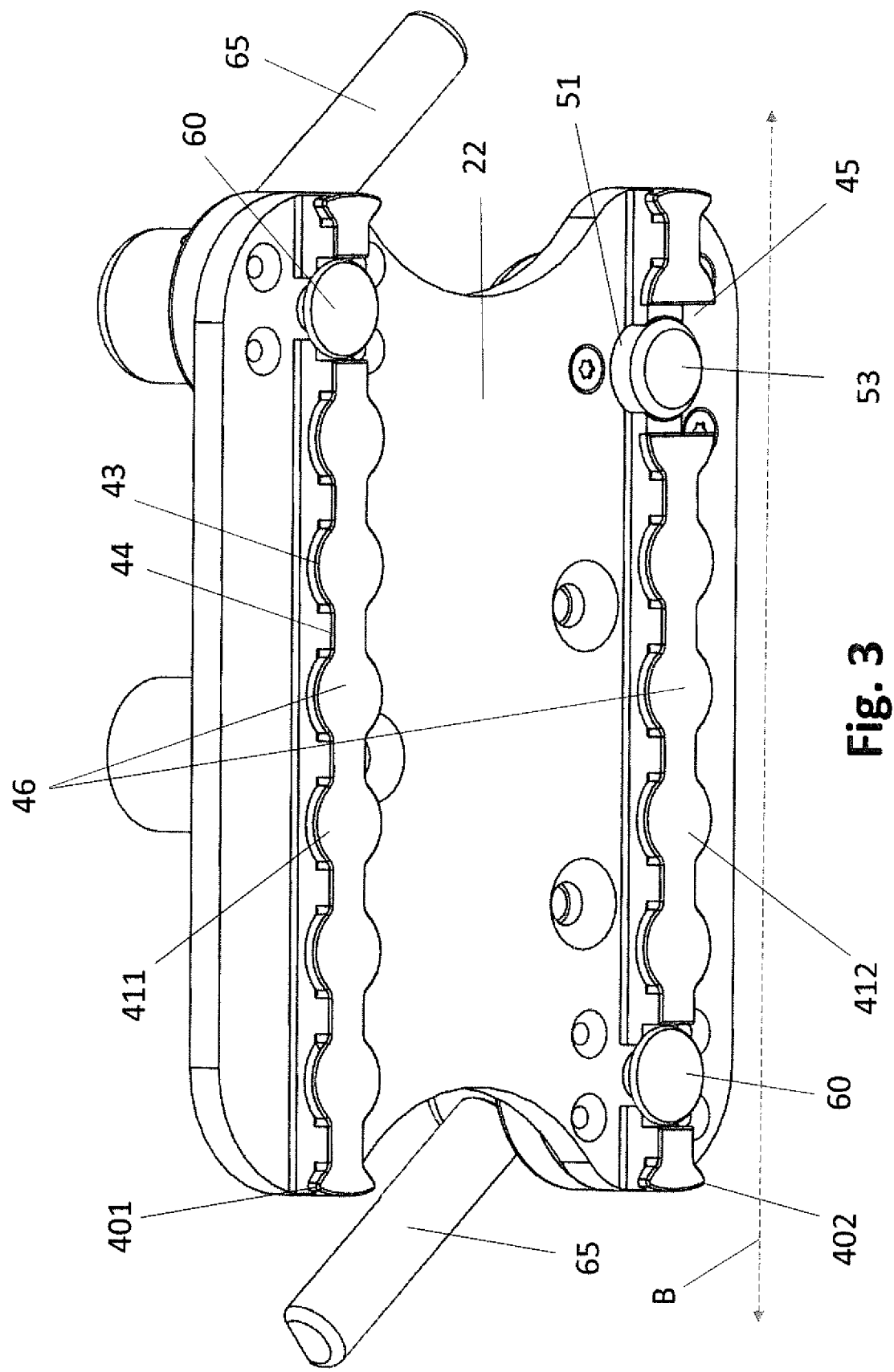
FIG. 3 shows a perspective view of the underside of the holding device from FIG. 1.

FIG. 3 shows a perspective view of the underside 53 of the holding device 10 from FIG. 1 and FIG. 2. In this view, a first guide element 401 with a first guide profile 411, and a second guide element 402 with a second guide profile 412 are visible, which are formed parallel to one another and along the longitudinal axis of the main body 21. The guide elements 401, 402 extend from the underside of the main body 21 in the insertion direction A, i.e. face substantially in a direction opposite to the direction in which the fixing means 23, locking means 50, and clamping means 60 are formed. The guide elements 401, 402 each have a guide profile 411, 412, which is configured such that it can cooperate with the mounting rail 30 (mounting rail 30 not illustrated in FIG. 3). Provision is made for the holding device 10 to be movable along the longitudinal axis of the mounting rail 30 as long as it is not been locked and/or clamped to the mounting rail 30. To this end, the first guide element 401 and the second guide element 402 are introduced into corresponding recessed regions of the mounting rail 30. As soon as the holding device has been introduced into the mounting rail 30 in this way, it can be moved in the guiding direction B relative to the rail. In the variant shown in FIG. 3, the guide elements 401, 402 extend along the entire length of the main body 21 of the holding device 10. However, embodiments can also be provided in which the at least one guide element 40 is formed in a longer or shorter manner.

In a holding device 10 according to the embodiment shown in FIG. 3, it may also be intended for the first guide element 401 to have a clearance 45 for receiving the locking means 50, and a clearance 45 for receiving the first clamping means 601, and for the second guide element 402 to have a clearance 45 for receiving the second clamping means 602. The clearances 45 of the guide elements 401, 402 can receive the clamping means 60 or locking means 50, respectively, in the guide elements 401, 402. This makes it possible for the clamping means 60 and the locking means 50 to be able to be moved from their first position into their second.

FIG. 3 also shows that the guide profiles 411, 412 of the guide elements 401, 402 have, in the guiding direction B, a profile pattern with regularly alternating wide portions 43 and narrow portions 44. The profile patterns, shown in FIG. 1, of the guides of the mounting rail 30 are in this case substantially complementary to the profile patterns of the guide profiles 411, 412 from FIG. 3. The guide profiles 411, 412 of the holding device 10 can thus be introduced into the mounting rail 30 without problems in the introduction direction A. The regularly alternating wide portions 43 and narrow portions 44 of the guide profiles 411, 412 (and thus also of the complementary guides of the mounting rail 30) have the positive effect that, as a result of the holding device 10 being moved in the guiding direction B, the holding device 10 is prevented from undesirably dropping out of the mounting rail 30. Only when the wide portions 43 and narrow portions 44 of the guide profile are made to coincide with the wide portions 43 and narrow portions 44 of the guide again can the holding device 10 be released from the mounting rail 30. The guide profiles 411, 412, shown in FIG. 3, with their narrow portions 44 and wide portions 43 thus allow initial fastening of the holding device 10 to the mounting rail 30.

FIG. 3 also shows an underside 53 of the locking means 50, wherein the locking means 50 is in its first locking position 51. In this position, the locking means 50 projects out of the main body 21 of the holding device 10 and into a recess in a guide element 401, 402. FIG. 3 shows by way of example an embodiment in which the locking means 50 projects into the second guide element 402. In this position, the locking means 50 can latch in place in a wide portion 43 of the guide of the mounting rail 30 (this not being shown in FIG. 3). This prevents the holding device 10 from being able to be moved along the mounting rail 30 in the guiding direction B.

In FIG. 3, a first clamping means 601 and a second clamping means 602 of the holding device 10 are shown. The first clamping device 601 and the second clamping device 602 each have a clamping face 63, which is formed parallel to the main face 22 of the main body 21. The clamping face is in the form of a flange and, in the case of the variant shown in FIG. 3, formed in a manner corresponding to the profile pattern of the guide elements 40. In an analogous manner to the locking means 50, the two clamping means 601, 602 are also in their first clamping position. In this position, the clamping face of the clamping element is at a smaller distance from the main body 21 than in the second clamping position. The clamping means 601, 602 clamps the holding device 10 immovably to the mounting rail 30 in the first clamping position.

As soon as the locking means 50 has been brought into its first position, it can engage or latch in place in a wide portion 43 of one of the guides of the mounting rail 30 (not shown in FIG. 3). Once the locking means 50 has latched in place, the profile patterns of the first and of the second guide element 401, 402 of the holding device 10 and the profile patterns of the guides of the mounting rail 30 are arranged in an offset manner with respect to one another. In this state, the clamping faces of the clamping means 601, 602 each coincide with a narrow portion 44 of a guide of the mounting rail 30. If the clamping means 601, 602 are now brought into their first position, the clamping faces 63 are moved in the direction of the main body 21 of the holding device 10 and in the direction of an inner wall of the guide until the clamping faces bear firmly against the inner wall. This causes the holding device 10 to be clamped to the mounting rail 30, this ensuring, in addition to the locking by the locking means 50, that the holding device 10 is fastened reliably to the mounting rail 30.

Figure 4:
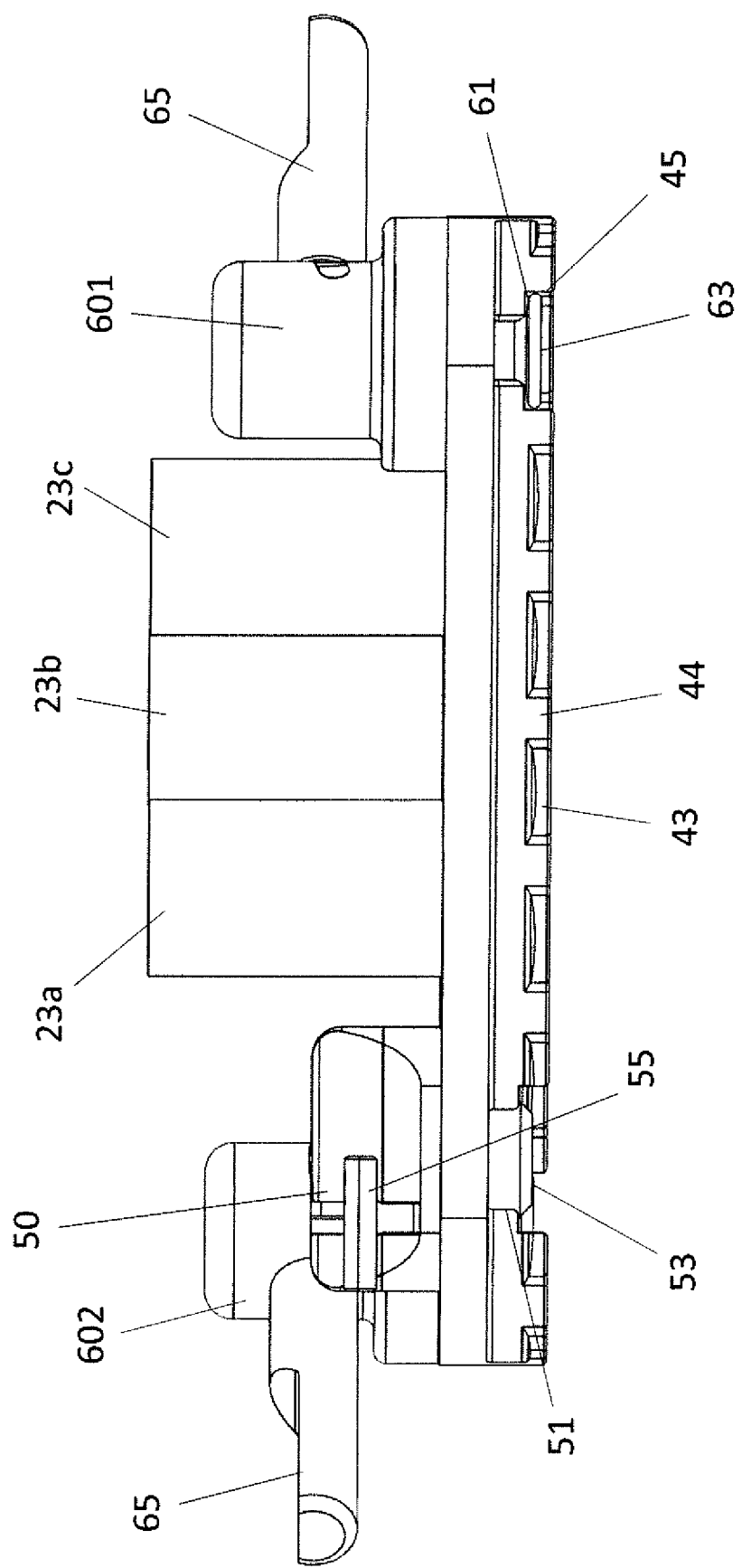
FIG. 4 shows a side view of a longitudinal side of the holding device from FIG. 1.
Figure 5:
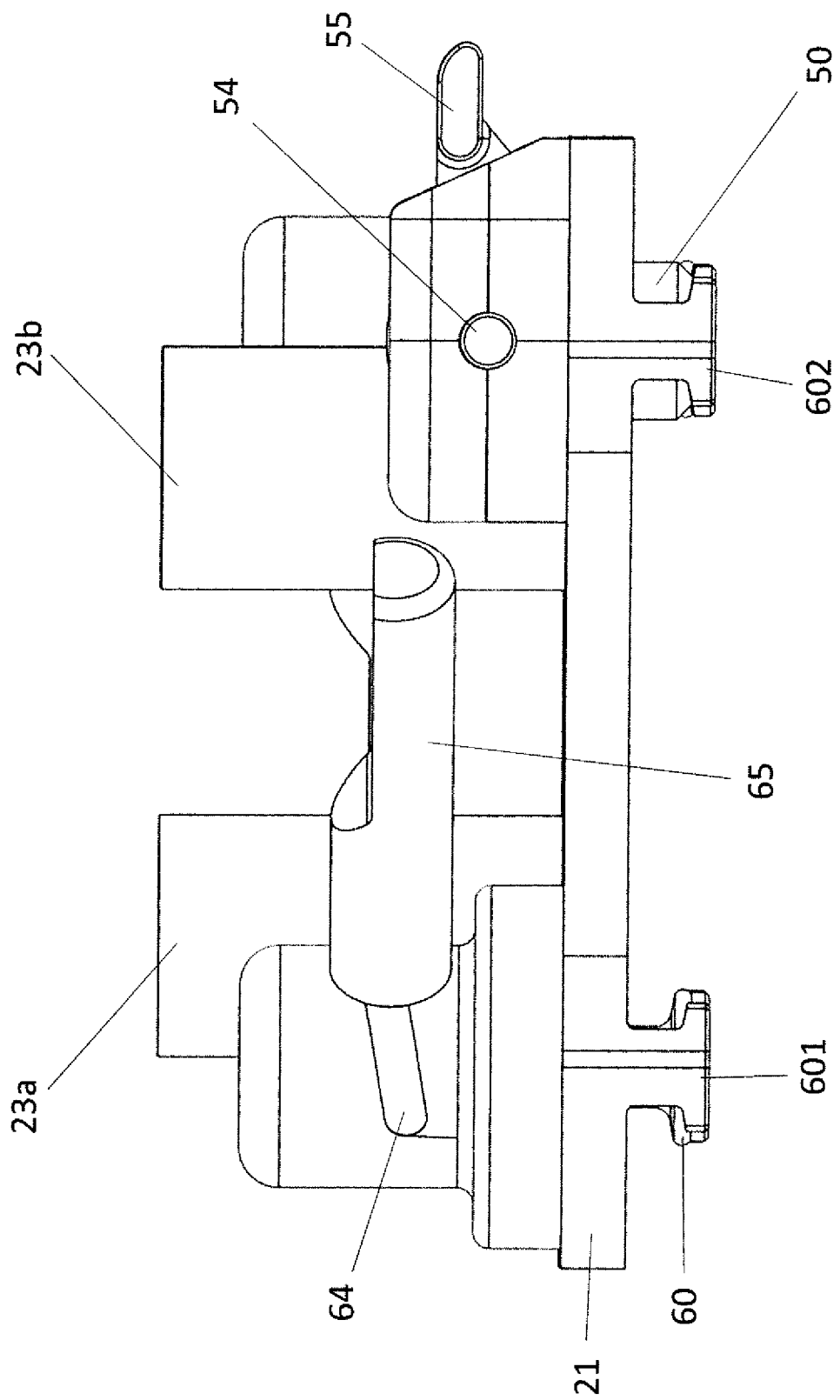
FIG. 5 shows a side view of a transverse side of the holding device from FIG. 1.

FIG. 4 and FIG. 5, which show a side view of a longitudinal side and of a transverse side, respectively, of the holding device from FIG. 1, FIG. 2 and FIG. 3, show, inter alia, the short distance of the clamping faces from the main body 21 of the device when the clamping means 601, 602 are each in their first clamping position. It is apparent in particular here that the clamping faces are at a shorter distance from the main face 22, in the first clamping position of the clamping means 601, 602, than the respective bottom faces 46 of the first and of the second guide profile 411, 412. In an analogous manner thereto, the locking means 50 also projects, in its first locking position 51, out of the main body only by an amount which is likewise less than the distance of the respective bottom faces 46 of the first and of the second guide profile 411, 412 from the main face 22.

Figure 6:
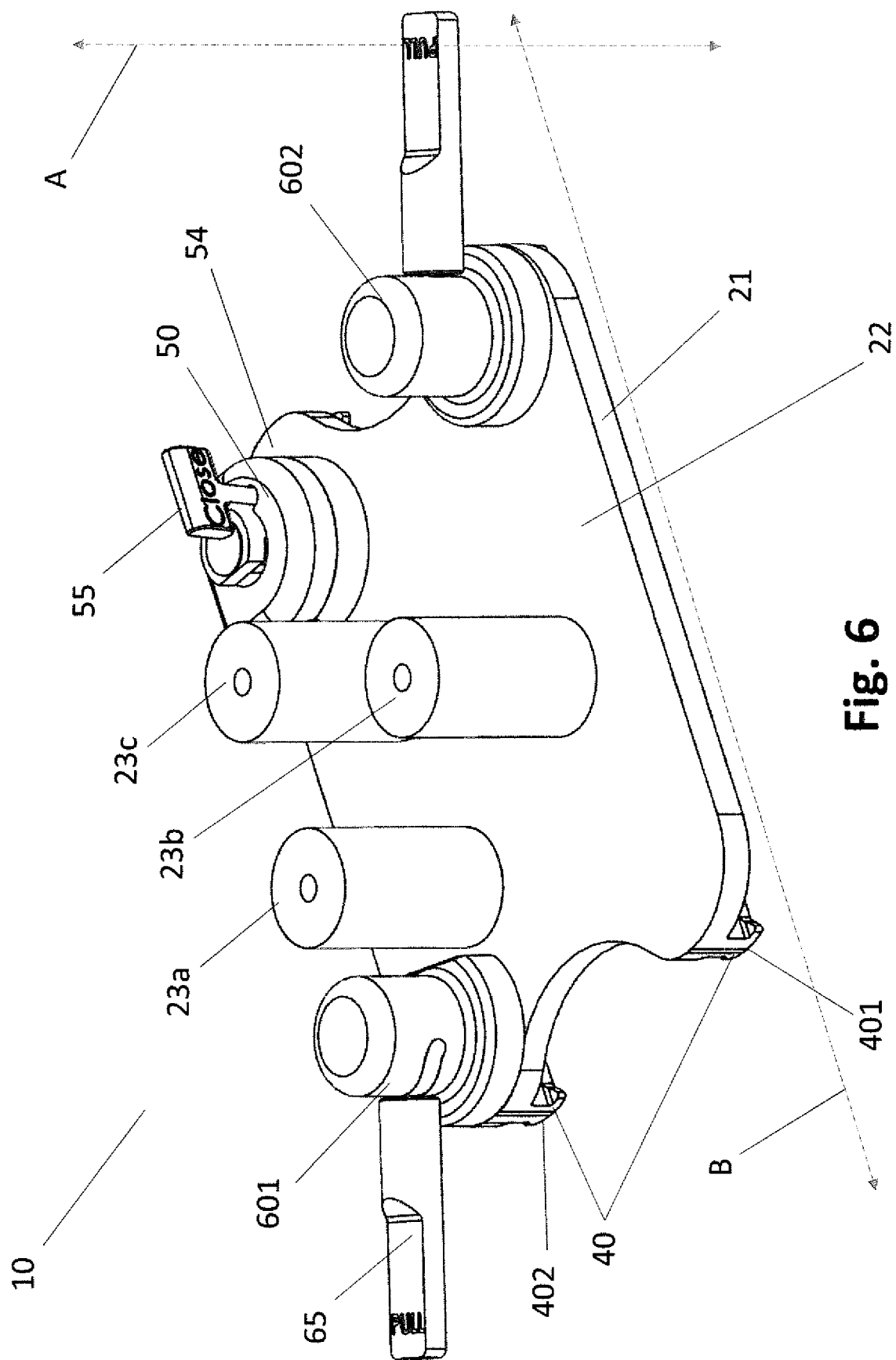
FIG. 6 shows a perspective view of a preferred embodiment of the holding device according to the invention for holding a portable medical appliance and for introducing into a mounting rail in the released state.

FIG. 6 shows a perspective view of a preferred embodiment of the holding device 10 according to the invention for holding a portable medical appliance and for introducing into a mounting rail 30 in the released state. In order to avoid repetitions, only the differences from the holding device 10 in the fixed state will be discussed in the following text.

A major difference of the released state, illustrated in FIG. 6, of the holding device 10 from the fixed state illustrated in FIGS. 1 to 5 concerns the positions of the fixing means 23a, b, c and of the locking means 50.

The toggle lever mechanism 54, shown in FIG. 6, of the locking means 50 is in an open state. The lever 55 is thus not recessed into the mount of the locking means 50 but projects out of the mount in a direction away from the main face 22 of the holding device 10. According to the embodiment shown by way of example, the lever 55 is raised such that it projects out of the mount more or less at right angles. The locking means 50, which is connected to the lever 55 of the toggle lever mechanism 54, is moved into the second locking position 52 by the lever 55 being raised. In this position, the holding device 10 is not locked to the mounting rail 30.

As is also shown in FIG. 6, the handle 65 of the rotary mechanism 64 of the first clamping means 601, and the handle 65 of the rotary mechanism of the second clamping means 602 are in a position which corresponds to the second position of the first clamping means 601 and of the second clamping means 602, respectively. The handles 65, which are each movable along the diagonally formed recess of the mount of each particular clamping means 601, 602 are, in the example in FIG. 6, in the position of the respectively smallest distance from the main body 21. Accordingly, the first clamping means 601 and the second clamping means 602, which are each connected to a handle 65, are each in their second clamping position. In the second clamping position, the clamping means 601, 602 are not clamped to the mounting rail 30. An advantage that arises from the toggle lever mechanism 54 and from the rotary mechanism 64 is the fact that the locking means 50 and the at least one clamping means 60, respectively, are actuated without additional tools.

If the locking means 50 is in its second locking position 52 and the first clamping means 601 and the second clamping means 602 are each in their second clamping position 62 (as in the example from FIG. 6), the holding device 10 can be moved along the mounting rail 30 in the guiding direction B.

Figure 7:
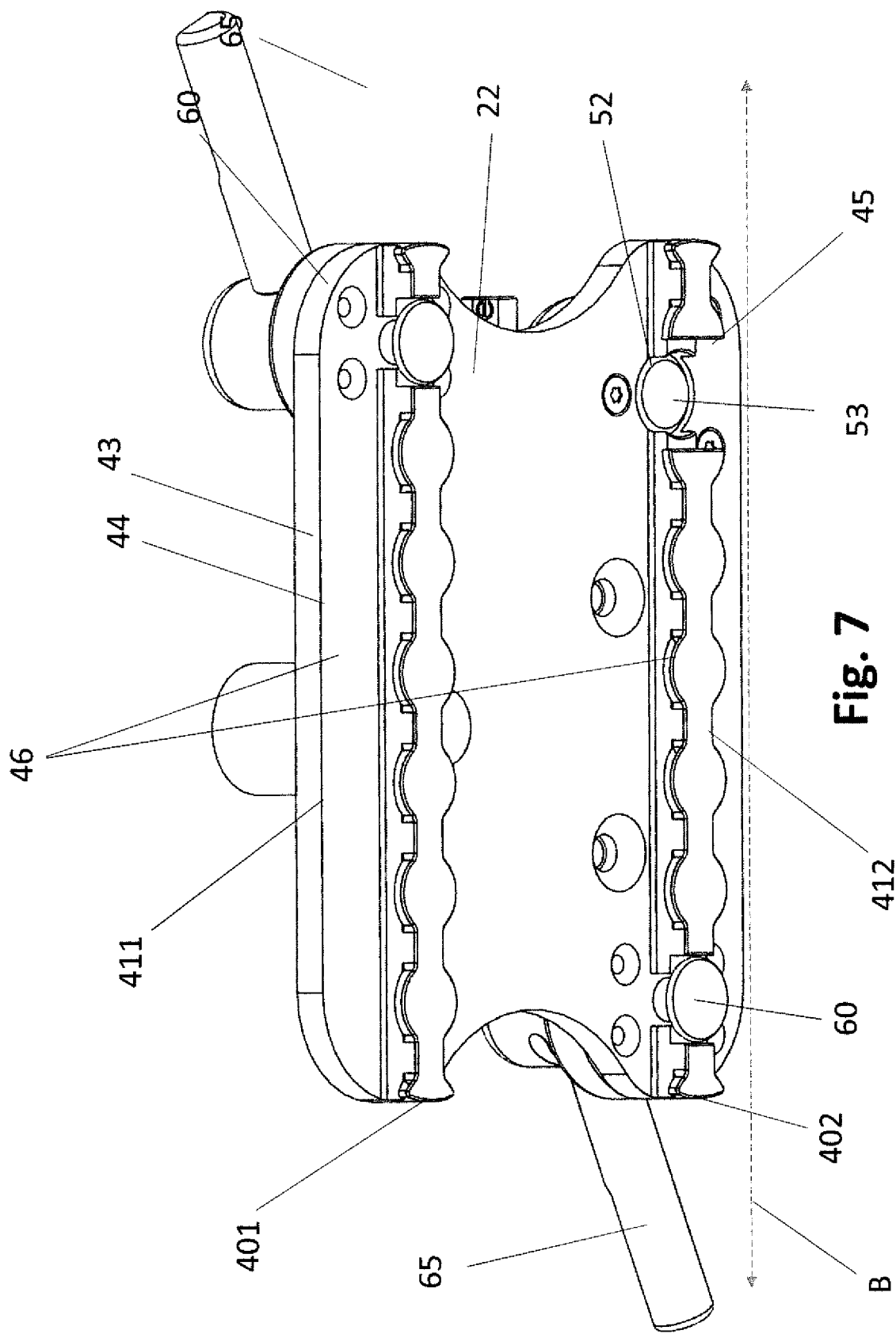
FIG. 7 shows a perspective view of the underside of the holding device from FIG. 6.

FIG. 7 shows a perspective view of the underside 53 of the holding device 10 from FIG. 6. In contrast to the clamped state, shown in FIGS. 1 to 5, of the holding device 10, the holding device 10 is in a released state in FIG. 6 and FIG. 7. In this state, the holding device 10 is movable along the mounting rail 30 in the guiding direction B. Accordingly, FIG. 7 shows that the first clamping means 601 and the second clamping means 602 are in a second clamping position 62. The first and the second guide element 401, 402 have clearances 45, in which the first clamping means 601 and the second clamping means 602, respectively, have been received in the region of the clamping faces 63. In the second clamping position 62, the clamping faces 63 of the clamping means 601, 602 are substantially flush with the bottom faces 46 of the guide profiles 411, 412 of the guide elements 40 in which they are received. As a result, it is possible to ensure that the holding device 10 can be guided and moved along the mounting rail 30 in the guiding direction B without problems, because a planar or smooth bottom face 46 of the guide profile 411, 412 reduces the friction that prevails between the region of the guide profile 411, 412 and the mounting rail 30 when the holding device 10 is moved in the guiding direction B relative to the mounting rail 30. According to the embodiment shown in FIGS. 1 to 7, provision is also made for the clearances 45 of the guide profile 411, 412 for receiving the clamping means 601, 602 each to be located in a region of the guide profile 411, 412 in which the profile pattern provides a wide portion 43. Thus, when the clamping means 60 are in their second clamping position 62, the clamping faces 63, together with the guide elements 40, form essentially a unitary guide profile 411, 412, which then has a clearance 45 only at that point that is provided for receiving the locking means 50.

FIG. 7 also shows the locking means 50 in a second locking position 52. The locking means 50 is positioned entirely within the main face 22 of the main body 21 in its second locking position 52. If the clamping means 60 are also in their second position, the holding device can be moved along the mounting rail 30 in the guiding direction B. Only when the locking means 50 is brought into the first position does it latch in place or engage in a wide portion 43 of the guide 31a, b of the mounting rail 30 and in this way prevent the holding device 10 from being able to be moved.

Figure 8:
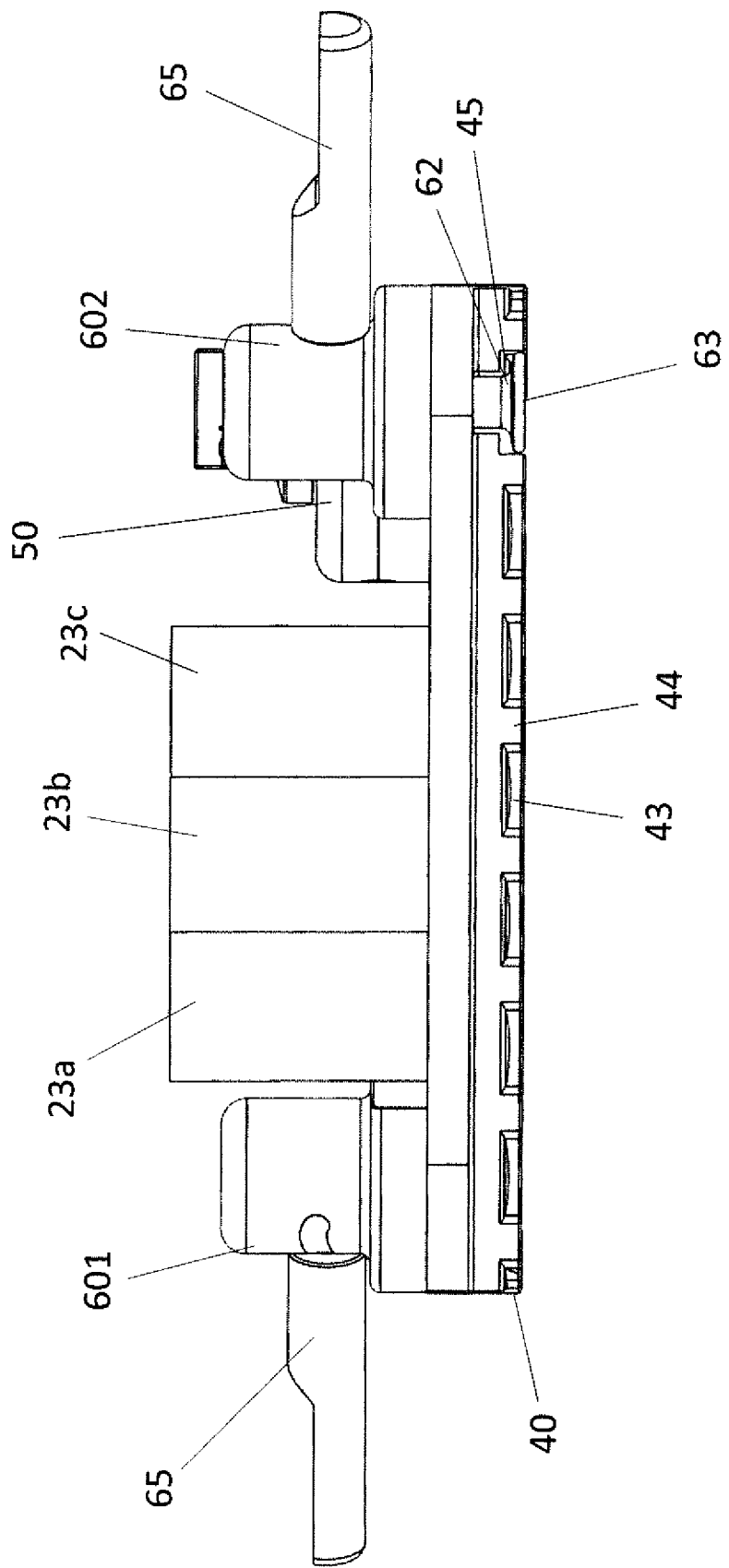
FIG. 8 shows a side view of a longitudinal side of the holding device from FIG. 6.

FIG. 8, which shows a side view of a longitudinal side of the holding device from FIG. 6 and FIG. 7, shows, inter alia, the long distance of the clamping faces from the main body 21 of the device when the at least one clamping means 60 is in each case in its second clamping position 62. It is apparent in particular here that the clamping faces 63, in the second clamping position 62 of the clamping means 60, are in each case flush with the bottom face 46 of the first and of the at least one guide profile. It is also apparent that the locking means 50, in its second locking position 52, is positioned entirely within the main face 22 of the main body 21. In this state, the holding device can be moved along the mounting rail 30 in the guiding direction B.

When the holding device 10 has been introduced into a mounting rail 30, it can first of all be moved along the rail in the guiding direction B as long as the clamping means 60 are in their second position 62 and the locking means 50 is in its second position 52. As soon as the locking means 50 is brought into its first position 51, it can engage or latch in place in a wide portion 43 of the at least one guide 31a, b of the mounting rail 30 when it is made to coincide with such a wide portion 43. Once the locking means 50 has latched in place, the profile pattern of the at least one guide element 40 of the holding device 10, and the profile pattern of the at least one guide 31a, b of the mounting rail 30 are arranged in an offset manner with respect to one another. This in turn has the result that the clamping face of the at least one clamping means 60 coincides with a narrow portion 44 of the at least one guide 31a, b of the mounting rail 30. If the clamping means 60 is now brought from its second position 62 into its first 61, the clamping face 63 is moved in the direction of the narrow portion until the clamping face 63 presses firmly against the narrow portion. This causes the holding device 10 to be clamped to the mounting rail 30, this ensuring, in addition to the locking by the locking means 50, that the holding device 10 is fastened reliably to the mounting rail 30.

FIG. 9 shows a perspective view of a clamping means 60 in a preferred embodiment. A mount, which has a diagonally extending recess, a handle 65, and the clamping face 63, which is in the form of a flange in the example in FIG. 9, can be seen. In the state shown, the handle 65 is in the uppermost region of the recess in the mount, i.e. at a point of the recess that is farthest from the lower end of the mount. If the handle 65 is brought into this position, the clamping means 60, which is connected to the handle 65, is lifted in the direction of the main body 21 (not illustrated in FIG. 9) such that the distance between the clamping face 63 and main body 21 is reduced—the clamping means 60 is then in its second position 62.

The invention is not limited to one of the above-described embodiments, but is modifiable in many ways.

All of the features and advantages, including structural details, spatial arrangements and method steps, that emerge from the claims, the description and the drawing can be essential to the invention both on their own and in a wide variety of combinations.

LIST OF REFERENCE SIGNS

| | |
|---|---|
| 10 | Holding device |
| 21 | Main body |
| 22 | Main face |
| 23a, b, c | Fixing means |
| 30 | Mounting rail |
| 31a, b | Guide |
| 40 | Guide element |
| 401 | First guide element |
| 402 | Second guide element |
| 411 | First guide profile |
| 412 | Second guide profile |
| 43 | Wide portion |
| 44 | Narrow portion |
| 45 | Clearance |
| 46 | Bottom face |
| 50 | Locking means |
| 51 | First locking position |
| 52 | Second locking position |
| 53 | Underside |
| 54 | Toggle lever mechanism |
| 55 | Lever |
| 60 | Clamping means |
| 601 | First clamping means |
| 602 | Second clamping means |
| 61 | First clamping position |
| 62 | Second clamping position |
| 63 | Clamping face |
| 64 | Rotary mechanism |
| 65 | Handle |
| A | Insertion direction (A) |
| B | Guiding direction (B) |

The invention claimed is:

1. A holding device for holding a portable medical appliance and for introducing into a mounting rail, the holding device comprising the following:
   a main body with a main face;
   at least one guide element having at least one guide profile, the at least one guide element being formed along a longitudinal axis of the main body and extending from the main body in an introduction direction, and the at least one guide element being introducible into a guide in the mounting rail;
   at least one fixing means for fixing the portable medical appliance to the holding device via an adapter;

a locking means that is movable at least partially in the introduction direction between a first locking position and a second locking position;

at least one clamping means, the at least one clamping means being movable at least partially in the introduction direction between a first clamping position and a second clamping position, wherein the at least one clamping means has a clamping face that is parallel to the main face of the main body, the clamping face being in the form of a flange, and the at least one guide profile has a bottom face, which is substantially parallel to the main face of the main body, and wherein the clamping face of the clamping means is more or less flush with the bottom face in the second clamping position.

2. The holding device as claimed in claim 1, wherein the at least one guide profile of the at least one guide element has, in a guiding direction, a profile pattern with regularly alternating first and second portions, the first portions wider than the second portions, the at least one guide profile having clearances for receiving the locking means and the at least one clamping means.

3. The holding device as claimed in claim 2, wherein the locking means of the holding device has the same cross profile as one of the first portions of the at least one guide profile.

4. The holding device as claimed in claim 2, wherein the clearance in the at least one guide element for receiving the locking means in the first locking position is located at least partially in a region of the at least one guide profile in which the profile pattern has the second portion.

5. The holding device as claimed in claim 2, wherein the clearance in the at least one guide profile for receiving the at least one clamping means is located at least partially in a region of the at least one guide profile in which the profile pattern has the first portion.

6. The holding device as claimed in claim 1, wherein the at least one guide element comprises a first guide element with a first guide profile, a second guide element with a second guide profile, wherein the at least one clamping means comprises a first clamping means, and a second clamping means, the first guide element having a clearance for receiving the locking means and a clearance for receiving the first clamping means, and the second guide element having a clearance for receiving the second clamping means.

7. The holding device as claimed in claim 1, wherein the locking means extends out of the main body in the introduction direction in the first locking position.

8. The holding device as claimed in claim 1, wherein an underside of the locking means is positioned entirely inside the main face of the main body in the second locking position.

9. The holding device as claimed in claim 1, wherein, in the first clamping position, the clamping face of the at least one clamping element is at a smaller distance from the main body than in the second clamping position, the at least one clamping means adapted to clamp the holding device immovably to the mounting rail in the first clamping position.

10. The holding device as claimed in claim 1, wherein the locking means has a toggle lever mechanism with a lever and a spring element, the locking means being able to be adjusted from the first locking position into the second locking position and/or from the second locking position into the first locking position via the toggle lever mechanism.

11. The holding device as claimed in claim 1, wherein the at least one clamping means has a rotary mechanism with a handle, via which the at least one clamping means can be adjusted from the first clamping position into the second clamping position and/or from the second clamping position into the first clamping position.

12. The holding device as claimed in claim 1, wherein the at least one fixing means is a threaded bolt.

* * * * *